(12) United States Patent
Beers et al.

(10) Patent No.: US 7,041,686 B2
(45) Date of Patent: May 9, 2006

(54) SUBSTITUTED IMIDAZOLES USEFUL IN THE TREATMENT OF INFLAMMATORY DISEASES

(76) Inventors: Scott Beers, 11 Kirkride Rd., Flemington, NJ (US) 08822; Michael P. Wachter, 52 North St., Bloomsbury, NJ (US) 08804

( * ) Notice: Subject to any disclaimer, the term of this patent is extended or adjusted under 35 U.S.C. 154(b) by 66 days.

(21) Appl. No.: 09/981,399

(22) Filed: Oct. 17, 2001

(65) Prior Publication Data

US 2004/0214816 A1 Oct. 28, 2004

Related U.S. Application Data

(60) Provisional application No. 60/241,256, filed on Oct. 18, 2000.

(51) Int. Cl.
  *A61K 31/4178* (2006.01)
  *A61K 31/4439* (2006.01)
  *C07D 401/14* (2006.01)
  *C07D 403/06* (2006.01)

(52) U.S. Cl. .................. 514/341; 514/397; 546/274.1; 548/314.7

(58) Field of Classification Search ............. 546/274.1; 548/314.7; 514/341, 397
See application file for complete search history.

(56) References Cited

U.S. PATENT DOCUMENTS 5,965,583 A   10/1999   Beers et al.
6,040,320 A    3/2000   Beers et al.

FOREIGN PATENT DOCUMENTS

WO   WO 93/14081 A1   7/1993
WO   WO 00/32598 A    6/2000

OTHER PUBLICATIONS

Boehm, Jeffrey C. et al., 1-Substituted 4-Aryl-5-pyridinylimidazoles: A New Class of Cytokine Suppressive Drugs with Low 5-Lipoxygenase and Cyclooxygenase Inhibitory Potency, J. Med Chem, 1996, 39 3929-37.

Badger, A.M. et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, The Journal of Pharmacology and Experimental Therapeutics, 1996, 279, 1453-61.

Griswold et al., Pharmacology of Cytokine Suppressive Anti-Inflammatory Drug Binding Protein (CSPB), A Novel Stress-Induced Kinase, Pharmacology Communications, 1996, 7, 323-29.

Elliot, M.J. et al., Treatment of Rheumatoid Arthritis with Chimeric Monoclonal Antibodies to Tumor Necrosis Factor Alpha, Arthritis & Rheumatism vol. 36, 1993, 1681-90.

Lantos et al., Synthetic and Mechanistic Studies on the Preparation of Pyridyl-Substituted Imidazothiazoles, The Journal of Organic Chemistry, vol. 53, 1988, p. 4223-27.

Dinarrello, Charles, A.., Inflammatory cytokines: interleukin-1 and tumor necrosis factor as effector molecules in autoimmune diseases, Current Opinion in Immunology, 1991, 3:941-948.

English Abstract—Japan Patent—JP63239274 (1988).
PCT Search Report for PCT/US 01/32436, Mar. 2002.

*Primary Examiner*—Laura L. Stockton

(57) ABSTRACT

This invention relates to substituted imidazoles of Formula I

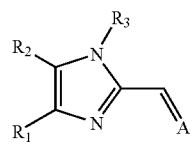

Formula I pharmaceutical compositions containing them, methods of using them and intermediates useful in their manufacture. The compounds of the invention modulate the production of a number of inflammatory cytokines and are useful in the treatment of diseases associated with the overproduction of inflammatory cytokines.

33 Claims, No Drawings

SUBSTITUTED IMIDAZOLES USEFUL IN THE TREATMENT OF INFLAMMATORY DISEASES

CROSS REFERENCE TO RELATED APPLICATION

This application claims the benefit of provisional application Ser. No. 60/241,256 filed on Oct. 18, 2000, the complete disclosure of which is hereby incorporated herein by reference for all purposes.

FIELD OF THE INVENTION

This invention relates to a series of substituted imidazoles, pharmaceutical compositions containing them and intermediates used in their manufacture. The compounds of the invention inhibit the production of a number of inflammatory cytokines, particularly, TNF-α, and IL-1β. Compounds of this invention are useful in the treatment of diseases associated with the overproduction of inflammatory cytokines.

BACKGROUND OF THE INVENTION

The inflammatory cytokines, IL-1β and TNF-α play an important role in a number of inflammatory diseases such as rheumatoid arthritis. C. Dinarello et al,. Inflammatory cytokines: Interleukin-1 and Tumor Necrosis Factor as Effector Molecules in Autoimmune Diseases *Curr. Opin. Immunol.* 1991, 3, 941–48. Arthritis is an inflammatory disease which affects millions of people and can strike at any joint of the human body. Its symptoms range from mild pain and inflammation in affected joints, to severe and debilitating pain and inflammation. Although the disease is associated mainly with aging adults, it is not restricted to adults. The most common arthritis therapy involves the use of nonsteroidal antiinflammatory drugs (NSAID) to alleviate the symptoms. However, despite their widespread use, many individuals cannot tolerate the doses necessary to treat the disease over a prolonged period of time. In addition, NSAIDs merely treat the symptoms of disease without affecting the underlying cause. Other drugs, such as methotrexate, gold salts, D-pencillamine, and prednisone are often used when patients fail to respond to NSAIDS. These drugs also have significant toxicities and their mechanism of action remain unknown.

Receptor antagonists to IL-1β and monoclonal antibodies to TNF-α have been shown to reduce symptoms of rheumatoid arthritis in small-scale human clinical trials. In addition to protein based therapies, there are small molecule agents which inhibit the production of these cytokines and have demonstrated activity in animal arthritis models. J. C. Boehm et al., 1-Substituted 4-Aryl-5-pyridinylimidazoles: A New Class of Cytokine Suppressive Drugs With Low 5-Lipoxygenase and Cyclooxygenase Inhibitory Potency, *J. Med. Chem.,* 1996, 39, 3929–37. Of these small molecule agents, SB 203580 has proved effective in reducing the production of TNF-α and IL-1 in LPS stimulated human monocyte cell lines with $IC_{50}$ values of 50 to 100 nM. J. Adams et al., Imidazole Derivatives And Their Use as Cytokine Inhibitor, International Patent application WO 93/14081, Jul. 23, 1993. In addition to this in vitro test, SB 203580 inhibits the production of the inflammatory cytokines in rats and mice at $IC_{50}$ values of 15 to 25 mg/kg. A. M. Badger, et al, Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics,* 1996, 279, 1453–61. Although human data is currently unavailable for SB 203580, monoclonal antibodies to TNF-α have proved efficacious in the treatment of rheumatoid arthritis. M. J. Elliot et al., Treatment of Rheumatoid Arthritis with Chimeric Monoclonal Antibodies to Tumor Necrosis Factor α, *Arthritis Rheum.* 1993 36, 1681–90. Due to SB 203580's oral activity and potency in animal models, researchers have suggested that a compound with this profile has potential as a viable treatment for rheumatoid arthritis. A. M. Badger, et al. Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics,* 1996, 279, 1453–61.

SB 203580 and other small molecule agents reduce the production of inflammatory cytokines by inhibiting the activity of a serine/threonin kinase p38 (note other researchers refer to this enzyme as CSBP), at an $IC_{50}$ of 200 nM. D. Griswold et al., Pharmacology of Cytokine Suppressive Anti-inflammatory Drug Binding Protein (CSPB), A Novel Stress-induced Kinase, *Pharmacology Communications,* 1996, 7, 323–29. Although the precise mechanism of this kinase is unknown, it has been implicated in both the production of TNF-α and the signaling responses associated with the TNF-α receptor.

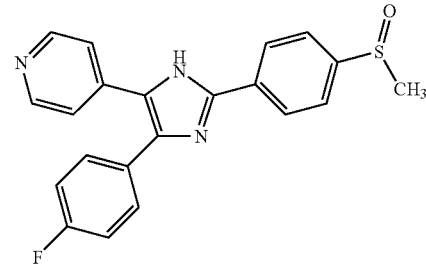

SB 203580

U.S. Pat. No. 5,965,583 (hereby incorporated by reference) describes substituted imidazoles of the formula:

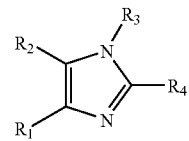

wherein $R_1$ is phenyl, substituted phenyl (where the substituents are selected from the group consisting of $C_{1-5}$alkyl, halogen, nitro, trifluoromethyl and nitrile), or heteroaryl where the heteroaryl contains 5 to 6 ring atoms; $R_2$ is phenyl, substituted phenyl (where the substituents are selected from the group consisting of $C_{1-5}$alkyl, halogen, nitro, trifluoromethyl and nitrile), heteroaryl where the heteroaryl contains 5 to 6 ring atoms and is optionally $C_{1-5}$alkyl substituted; $R_3$ is hydrogen, SEM, $C_{1-5}$alkoxycarbonyl, aryloxycarbonyl, aryl$C_{1-5}$alkyloxycarbonyl, aryl$C_{1-5}$alkyl, substituted aryl$C_{1-}$ salkyl (where the aryl substituents are independently selected from one or more members of the group consisting of $C_{1-5}$alkyl, $C_{1-5}$alkoxy, halogen, amino, $C_{1-5}$alkylamino, and $diC_{1-5}$alkylamino), phthalimido$C_{1-5}$alkyl, amino$C_{1-5}$alkyl, diamino$C_{1-5}$alkyl, succinimido$C_{1-5}$alkyl, $C_{1-5}$alkylcarbonyl, arylcarbonyl, $C_{1-5}$alkylcarbonyl$C_{1-5}$alkyl, aryloxycarbonyl$C_{1-5}$alkyl, heteroaryl$C_{1-5}$alkyl where the heteroaryl contains 5 to 6 ring atoms; $R_4$ is —A—$(CH_2)_q$—X wherein A is vinylene, ethynylene or

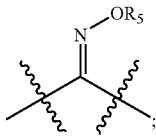

where $R_5$ is selected from the group consisting of hydrogen, $C_{1-5}$alkyl, phenyl and phenyl$C_{1-5}$alkyl; q is 0–9; X is selected from the group consisting of hydrogen, hydroxy, vinyl, substituted vinyl (where one or more substituents are selected from the group consisting of fluorine, bromine, chlorine and iodine), ethynyl, substituted ethynyl (where the substituents are selected from one or more members of the group consisting of fluorine, bromine, chlorine and iodine), $C_{1-5}$alkyl, substituted $C_{1-5}$alkyl (where the alkyl substituents are selected from the group consisting of one or more $C_{1-5}$alkoxy, trihaloalkyl, phthalimido and amino), $C_{3-7}$cycloalkyl, $C_{1-5}$alkoxy, substituted $C_{1-5}$alkoxy (where the alkyl substituents are selected from the group consisting of phthalimido and amino), phthalimidooxy, phenoxy, substituted phenoxy (where the phenyl substituents are selected from the group consisting of $C_{1-5}$alkyl, halogen and $C_{1-5}$alkoxy), phenyl, substituted phenyl (where the phenyl substituents are selected from the group consisting of $C_{1-5}$alkyl, halogen and $C_{1-5}$alkoxy), aryl$C_{1-5}$alkyl, substituted aryl$C_{1-5}$alkyl (where the aryl substituents are selected from the group consisting of $C_{1-5}$alkyl, halogen and $C_{1-5}$alkoxy), amino, $C_{1-5}$alkylamino, $diC_{1-5}$alkylamino, nitrile, oxime, benzyloxyimino, $C_{1-5}$alkyloxyimino, phthalimido, succinimido, $C_{1-5}$alkylcarbonyloxy, phenylcarbonyloxy, substituted phenylcarbonyloxy (where the phenyl substituents are selected from the group consisting of $C_{1-5}$alkyl, halogen and $C_{1-5}$alkoxy), phenyl$C_{1-5}$alkylcarbonyloxy (where the phenyl substituents are selected from the group consisting of $C_{1-5}$alkyl, halogen and $C_{1-5}$alkoxy), aminocarbonyloxy, $C_{1-5}$alkylaminocarbonyloxy, $diC_{1-5}$alkylaminocarbonyloxy, $C_{1-5}$alkoxycarbonyloxy, substituted $C_{1-5}$alkoxycarbonyloxy (where the alkyl substituents are selected from the group consisting of methyl, ethyl, isopropyl and hexyl), phenoxycarbonyloxy, substituted phenoxycarbonyloxy (where the phenyl substituents are selected from the group consisting of $C_{1-5}$alkyl, $C_{1-5}$alkoxy and halogen), $C_{1-5}$alkylthio, substituted $C_{1-5}$alkylthio (where the alkyl substituents are selected from the group consisting of hydroxy and phthalimido), $C_{1-5}$akylsulfonyl, phenylsulfonyl, substituted phenylsulfonyl (where the phenyl substituents are selected from the group consisting of bromine, fluorine, chlorine, $C_{1-5}$alkoxy and trifluoromethyl); with the proviso: if A is

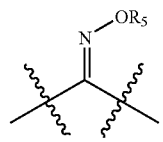

q is 0 and X is H, $R_3$ may not be SEM; and pharmaceutically acceptable salts thereof as useful in the treatment of diseases associated with the overproduction of inflammatory cytokines.

U.S. Pat. No. 6,040,320 (hereby incorporated by reference) also describes substituted imidazoles of the formula:

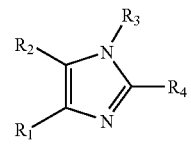

wherein $R_1$ is phenyl, heteroaryl wherein the heteroaryl contains 5 to 6 ring atoms, or substituted phenyl wherein the substituents are independently selected from one or members of the group consisting of $C_{1-5}$alkyl, halogen, nitro, trifluoromethyl and nitrile; $R_2$ is phenyl, heteroaryl wherein the heteroaryl contains 5 to 6 ring atoms, substituted heteroaryl wherein the substituents are independently selected from one or more members of the group consisting of $C_{1-5}$alkyl and halogen, or substituted phenyl wherein the substituents are independently selected from one or members of the group consisting of $C_{1-5}$alkyl, halogen, nitro, trifluoromethyl and nitrile; $R_3$ is hydrogen, SEM, $C_{1-5}$alkoxycarbonyl, aryloxycarbonyl, aryl$C_{1-5}$alkyloxycarbonyl, aryl$C_{1-5}$alkyl, phthalimido$C_{1-5}$alkyl, amino$C_{1-5}$alkyl, diamino$C_{1-5}$alkyl, succinimido$C_{1-5}$alkyl, $C_{1-5}$alkylcarbonyl, arylcarbonyl, $C_{1-5}$alkylcarbonyl$C_{1-5}$alkyl, aryloxycarbonyl$C_{1-5}$alkyl, heteroaryl$C_{1-5}$alkyl where the heteroaryl contains 5 to 6 ring atoms, or substituted aryl$C_{1-5}$alkyl wherein the aryl substituents are independently selected from one or more members of the group consisting of $C_{1-5}$alkyl, $C_{1-5}$alkoxy, halogen, amino, $C_{1-5}$alkylamino, and $diC_{1-5}$alkylamino; $R_4$ is $(A)_n$—$(CH_2)_q$—X wherein A is sulfur or carbonyl; n is 0 or 1; q is 0–9; X is selected from the group consisting of hydrogen, hydroxy, halogen, vinyl, ethynyl, $C_{1-5}$alkyl, $C_{3-7}$cycloalkyl, $C_{1-5}$alkoxy, phenoxy, phenyl, aryl$C_{1-5}$alkyl, amino, $C_{1-5}$alkylamino, nitrile, phthalimido, amido, phenylcarbonyl, $C_{1-5}$alkylaminocarbonyl, phenylaminocarbonyl, aryl$C_{1-5}$alkylaminocarbonyl, $C_{1-5}$alkylthio, $C_{1-5}$alkylsulfonyl, phenylsulfonyl, substituted sulfonamido wherein the sulfonyl substituent is selected from the group consisting of $C_{1-5}$alkyl, phenyl, aryl$C_{1-5}$alkyl, thienyl, furanyl, and naphthyl; substituted vinyl wherein the substituents are independently selected from one or members of the group consisting of fluorine, bromine, chlorine and iodine, substituted ethynyl wherein the substituents are independently selected from one or more members of the group consisting of fluorine, bromine, chlorine and iodine, substituted $C_{1-5}$alkyl wherein the substituents are selected from the group consisting of one or more $C_{1-5}$alkoxy, trihaloalkyl, phthalimido and amino, substituted phenyl wherein the phenyl substituents are independently selected from one or more members of the group consisting of $C_{1-5}$alkyl, halogen and $C_{1-5}$alkoxy, substituted phenoxy wherein the phenyl substituents are independently selected from one or more members of the group consisting of $C_{1-5}$alkyl, halogen and $C_{1-5}$alkoxy, substituted $C_{1-5}$alkoxy wherein the alkyl substituent is selected from the group consisting of phthalimido and amino, substituted aryl$C_{1-5}$alkyl wherein the alkyl substituent is hydroxyl, substituted aryl$C_{1-5}$alkyl wherein the phenyl substituents are independently selected from one or more members of the group consisting of $C_{1-5}$alkyl, halogen and $C_{1-5}$alkoxy, substituted amido wherein the carbonyl substituent is selected from the group consisting of $C_{1-5}$alkyl, phenyl, aryl$C_{1-5}$alkyl, thienyl, furanyl, and naphthyl, substituted phenylcarbonyl wherein the phenyl substituents are independently selected from one or members of the group consisting of $C_{1-5}$alkyl, halogen and $C_{1-5}$alkoxy, substituted $C_{1-5}$alkylthio wherein the alkyl substituent is selected from the group consisting of hydroxy and phthalimido, substituted $C_{1-5}$alkylsulfonyl wherein the alkyl substituent is selected from the group consisting of hydroxy and phthalimido, substituted phenylsulfonyl wherein the phenyl substituents are independently selected from one or members of the group consisting of bromine, fluorine, chlorine, $C_{1-5}$alkoxy and trifluoromethyl, with the proviso: if A is sulfur and X is other than hydrogen, $C_{1-5}$alkylaminocarbonyl, phenylaminocarbonyl, aryl$C_{1-5}$alkylaminocarbonyl, $C_{1-5}$alkylsulfonyl or phenylsulfonyl, then q must be equal to or greater than 1; if A is sulfur and q is 1, then X cannot be $C_{1-2}$alkyl; if A is carbonyl and q is 0, then X cannot be vinyl, ethynyl, $C_{1-5}$alkylaminocarbonyl, phenylaminocarbonyl, aryl$C_{1-5}$alkylaminocarbonyl, $C_{1-5}$alkylsulfonyl or phenylsulfonyl; if A is carbonyl, q is 0 and X is H, then $R_3$ is not SEM; if n is 0 and q is 0, then X cannot be hydrogen; and pharmaceutically acceptable salts thereof as useful in the treatment of diseases associated with the overproduction of inflammatory cytokines.

The object of the present invention is to provide a series of substituted imidazoles, pharmaceutical compositions containing them and intermediates used in their manufacture. Another object is to provide a method for treating diseases associated with the overproduction of inflammatory cytokines.

SUMMARY OF THE INVENTION

The invention relates to compounds of Formula I:

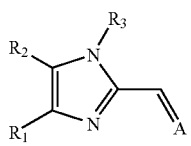

Formula I wherein:

$R_1$ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms);

$R_2$ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms and is optionally substituted with one to four substituents independently selected from the group consisting of $C_{1-5}$alkyl and halogen);

$R_3$ is selected from the group consisting of hydrogen, $C_{1-5}$alkyl, aryl$C_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl)), heteroaryl$C_{1-5}$alkyl (wherein heteroaryl contains 5 to 6 ring atoms), amino$C_{1-5}$alkyl, diamino$C_{1-5}$alkyl, phthalimido$C_{1-5}$alkyl, succinimido$C_{1-5}$alkyl, SEM, $C_{1-5}$alkylcarbonyl, $C_{1-5}$alkylcarbonyl$C_{1-5}$alkyl, $C_{1-5}$alkoxycarbonyl, arylcarbonyl, aryloxycarbonyl, aryl$C_{1-5}$alkyloxycarbonyl and aryloxycarbonyl$C_{1-5}$alkyl;

A is a five to seven member heterocyclyl ring optionally substituted with one to two substituents independently selected from X; wherein the ring has an unsaturated bond of attachment at a ring carbon atom; has a ring nitrogen atom substituted with a substituent selected from W adjacent to the ring carbon of attachment; has a ring carbon atom adjacent to the ring carbon of attachment; optionally has 1 or 2 double bonds formed in the ring between adjacent ring members; and, optionally has 1 or 2 ring members independently selected from the group consisting of O, N and S;

W is a substituent selected from the group consisting of hydrogen, $C_{1-5}$alkyl, $C_{1-5}$alkoxy, amino$C_{1-5}$alkyl (wherein amino is optionally substituted with one to two substituents independently selected from $C_{1-5}$alkyl), aryl$C_{1-5}$alkyl and heteroaryl$C_{1-5}$alkyl (wherein the aryl, heteroaryl and $C_{1-5}$alkyl portions of any of the foregoing substituents are optionally substituted with one to three substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile); and, X is a substituent selected from the group consisting of $C_{1-5}$alkyl, $C_{1-5}$alkenyl, $C_{1-5}$alkynyl, $C_{1-5}$alkoxy, amino (wherein amino is optionally substituted with one to two substituents independently selected from $C_{1-5}$alkyl), amino$C_{1-5}$alkyl (wherein amino is optionally substituted with one to two substituents independently selected from $C_{1-5}$alkyl), aryl, aryl$C_{1-5}$alkyl, heteroaryl and heteroaryl$C_{1-5}$alkyl (wherein the aryl, heteroaryl and $C_{1-5}$alkyl portions of any of the foregoing substituents are optionally substituted with one to two substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile);

and pharmaceutically acceptable salts thereof.

The present invention includes a method for preparing a compound of Formula I:

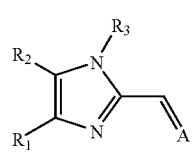

Formula I wherein
R₁ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms);

R₂ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms and is optionally substituted with one to four substituents independently selected from the group consisting of $C_{1-5}$alkyl and halogen);

R₃ is selected from the group consisting of hydrogen, $C_{1-5}$alkyl, aryl$C_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl)), heteroaryl$C_{1-5}$alkyl (wherein heteroaryl contains 5 to 6 ring atoms), amino$C_{1-5}$alkyl, diamino$C_{1-5}$alkyl, phthalimido$C_{1-5}$alkyl, succinimido$C_{1-5}$alkyl, SEM, $C_{1-5}$alkylcarbonyl, $C_{1-5}$alkylcarbonyl$C_{1-5}$alkyl, $C_{1-5}$alkoxycarbonyl, arylcarbonyl, aryloxycarbonyl, aryl$C_{1-5}$alkyloxycarbonyl and aryloxycarbonyl$C_{1-5}$alkyl;

A is a five to seven member heterocyclyl ring optionally substituted with one to two substituents independently selected from X; wherein the ring has an unsaturated bond of attachment at a ring carbon atom; has a ring nitrogen atom substituted with a substituent selected from W adjacent to the ring carbon of attachment; has a ring carbon atom adjacent to the ring carbon of attachment; optionally has 1 or 2 double bonds formed in the ring between adjacent ring members; and, optionally has 1 or 2 ring members independently selected from the group consisting of O, N and S;

W is a substituent selected from the group consisting of hydrogen, $C_{1-5}$alkyl, $C_{1-5}$alkoxy, amino$C_{1-5}$alkyl (wherein amino is optionally substituted with one to two substituents independently selected from $C_{1-5}$alkyl), aryl$C_{1-5}$alkyl and heteroaryl$C_{1-5}$alkyl (wherein the aryl, heteroaryl and $C_{1-5}$alkyl portions of any of the foregoing substituents are optionally substituted with one to three substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile); and, X is a substituent selected from the group consisting of $C_{1-5}$alkyl, $C_{1-5}$alkenyl, $C_{1-5}$alkynyl, $C_{1-5}$alkoxy, amino (wherein amino is optionally substituted with one to two substituents independently selected from $C_{1-5}$alkyl), amino$C_{1-5}$alkyl (wherein amino is optionally substituted with one to two substituents independently selected from $C_{1-5}$alkyl), aryl, aryl$C_{1-5}$alkyl, heteroaryl and heteroaryl$C_{1-5}$alkyl (wherein the aryl, heteroaryl and $C_{1-5}$alkyl portions of any of the foregoing substituents are optionally substituted with one to two substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile);

and pharmaceutically acceptable salts thereof; comprising, converting an intermediate compound of Formula II

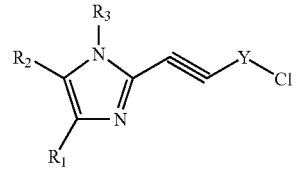

Formula II wherein
Y is a three to five member linear alkylene, alkenylene, heteroalkylene or heteroalkenylene chain optionally substituted with one to two substituents independently selected from X; wherein the alkenylene and heteroalkenylene chain has 1 or 2 double bonds formed in the chain between adjacent members; and, wherein the heteroalkylene and heteroalkenylene chain has 1 or 2 members independently selected from the group consisting of O, N and S; and, all other substituents are as previously defined;

by ammonolysis, using an excess of a compound selected from H₂N(W) in an appropriate solvent, to form a secondary amine intermediate of Formula III; and,

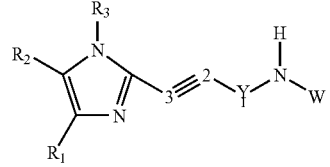

Formula III coupling the amine at the 2 position of the triple bond by a Michael addition, in the presence of appropriate reagents and solvents, to form the compound of Formula I.

The present invention also includes an intermediate compound of Formula II:

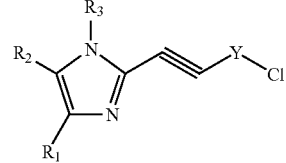

Formula II wherein
R₁ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms);

R₂ is selected from the group consisting of phenyl (optionally substituted with one to five substituents independently selected from the group consisting of $C_{1-5}$alkyl, ;halogen, nitro, trifluoromethyl and nitrile) and heteroaryl (wherein heteroaryl contains 5 to 6 ring atoms and is optionally substituted with one to four substituents independently selected from the group consisting of $C_{1-5}$alkyl and halogen);

$R_3$ is selected from the group consisting of hydrogen, $C_{1-5}$alkyl, aryl$C_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl)), heteroaryl$C_{1-5}$alkyl (wherein heteroaryl contains 5 to 6 ring atoms), amino$C_{1-5}$alkyl, diamino$C_{1-5}$alkyl, phthalimido$C_{1-5}$alkyl, succinimido$C_{1-5}$alkyl, SEM, $C_{1-5}$alkylcarbonyl, $C_{1-5}$alkylcarbonyl$C_{1-5}$alkyl, $C_{1-5}$alkoxycarbonyl, arylcarbonyl, aryloxycarbonyl, aryl$C_{1-5}$alkyloxycarbonyl and aryloxycarbonyl$C_{1-5}$alkyl; and, Y is a three to five member linear alkylene, alkenylene, heteroalkylene or heteroalkenylene chain optionally substituted with one to two substituents independently selected from X; wherein the alkenylene and heteroalkenylene chain has 1 or 2 double bonds formed in the chain between adjacent members; and, wherein the heteroalkylene and heteroalkenylene chain has 1 or 2 members independently selected from the group consisting of O, N and S;

with the proviso that Y cannot be selected from $(CH_2)_3$;

and pharmaceutically acceptable salts thereof.

DETAILED DESCRIPTION OF THE INVENTION

The compounds of the present invention are useful as inhibitors of TNF-α and IL-1. Some of the instant compounds are more active than others and, thereby, have a structure activity relationship that may be preferred, more preferred or most preferred.

Compounds of Formula I that are preferred include a compound wherein:

$R_1$ is phenyl (optionally substituted with one to five substituents independently selected from the group consisting of $C_{1-5}$alkyl and halogen);

more preferably, $R_1$ is phenyl substituted with a substituent selected from halogen;

and, most preferably, $R_1$ is phenyl substituted with fluorine.

Other compounds of Formula I that are preferred include a compound wherein:

$R_2$ is heteroaryl (wherein heteroaryl contains 5 to 6 ring atoms and is optionally substituted with one to four substituents independently selected from the group consisting of $C_{1-5}$alkyl and halogen);

more preferably, $R_2$ is selected from the group consisting of 2-furyl, 3-furyl, 2-thienyl, 3-thienyl, 2-pyrrolyl, 3-pyrrolyl, 2-pyrrolinyl, 3-pyrrolinyl, 4-pyrrolinyl, 5-pyrrolinyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-imidazolinyl, 4-imidazolinyl, 5-imidazolinyl, 3-pyrazolyl, 4-pyrazolyl, 5-pyrazolyl, 3-pyrazolinyl, 4-pyrazolinyl, 5-pyrazolinyl, 3-isoxazolyl, 4-isoxazolyl, 5-isoxazolyl, 3-isothiazolyl, 4-isothiazolyl, 5-isothiazolyl, 4-1,2,3-oxadiazolyl, 5-1,2,3-oxadiazolyl, 4-1,2,3-triazolyl, 5-1,2,3-triazolyl, 2-1,3,4-thiadiazolyl, 5-1,3,4-thiadiazolyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 3-pyrazinyl and 2-1,3,5-triazinyl optionally substituted with one substituent selected from $C_{1-5}$alkyl; and, most preferably, $R_2$ is selected from the group consisting of 4-pyridinyl, 4-pyrimidinyl and (2-butyl)pyridin-4-yl.

Embodiments of compounds of Formula I that are preferred also include a compound wherein:

$R_3$ is selected from the group consisting of hydrogen, $C_{1-5}$alkyl and aryl$C_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl));

more preferably, $R_3$ is selected from the group consisting of hydrogen and phenyl$C_{1-5}$alkyl (wherein phenyl is optionally substituted with one substituent selected from $C_{1-5}$alkoxy); and, most preferably, $R_3$ is selected from the group consisting of benzyl, phenethyl and phenylpropyl.

Other preferred embodiments of compounds of Formula I include a compound wherein:

A is selected from the group consisting of pyrrolidinyl, imidazolidinyl, pyrazolidinyl, piperidinyl, morpholinyl, thiomorpholinyl, piperazinyl, hexahydro-1H-azepine, hexahydro-1H-1,3-diazepine, hexahydro-1,3-oxazepine, hexahydro-1,3-thiazepine and hexahydro-1H-1,3,5-triazepine; and, more preferably, A is selected from the group consisting of pyrrolidinyl, imidazolidinyl, pyrazolidinyl, piperidinyl and piperazinyl.

Additional compounds of Formula I that are preferred include a compound wherein:

W is a substituent selected from the group consisting of hydrogen, $C_{1-5}$alkyl and $C_{1-5}$alkoxy (wherein $C_{1-5}$alkyl for any of the foregoing substituents is optionally substituted with one to three substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile);

more preferably, W is a substituent selected from the group consisting of hydrogen and $C_{1-5}$alkyl; and, most preferably, W is a substituent selected from the group consisting of hydrogen, methyl, ethyl, n-propyl, i-propyl, n-butyl and t-butyl.

Preferred embodiments of compounds of Formula I also include a compound wherein:

X is a substituent selected from the group consisting of $C_{1-5}$alkyl, $C_{1-5}$alkenyl, $C_{1-5}$alkynyl, $C_{1-5}$alkoxy and amino (wherein amino is optionally substituted with one to two substituents independently selected from $C_{1-5}$alkyl);

more preferably, X is a substituent selected from $C_{1-5}$alkyl; and, most preferably, X is a substituent selected from the group consisting of methyl, ethyl, n-propyl, i-propyl, n-butyl and t-butyl.

The preferred compounds of Formula I include a compound of formula:

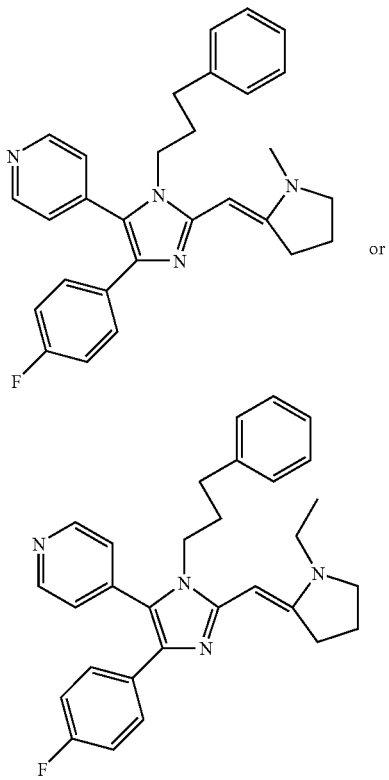

or and pharmaceutically acceptable salts thereof.

In a preferred embodiment of the method of the present invention, Y is a three to five member linear alkylene chain optionally substituted with one to two substituents independently selected from X. In a more preferred embodiment of the instant method, Y is an unsubstituted three to five member linear alkylene chain.

In a preferred embodiment of the intermediate compound of Formula II, Y is a four to five member linear alkylene chain optionally substituted with one to two substituents independently selected from X. In a more preferred embodiment of the instant compound, Y is an unsubstituted four to five member linear alkylene chain.

The terms used in describing the invention are commonly used and known to those skilled in the art. However, the terms that could have other meanings are defined. The term "independently" means that when there are more than one substituent, the substituents may be different.

The term "alkyl" refers to straight and branched-chain alkyl groups; "alkoxy" refers O-alkyl where alkyl is as defined supra. The term cycloalkyl refers to a cyclic alkyl ring of five to seven carbon atom members. Examples of such cyclic alkyl rings include pentyl, hexyl or heptyl.

In the present invention, the term heterocyclyl refers to the "A" substituent which comprises a cyclic alkyl ring of five to seven members wherein at least one member is a first nitrogen atom substituted with a substituent selected from W.

The heterocyclyl ring may contain up to two heteroatoms independently selected from the group consisting of nitrogen, oxygen and sulfur. Up to two carbon atom ring members may be optionally substituted with one to two substituents selected from X or may have empty valences satisfied by the ring itself. Nitrogen atom ring members in addition to the first nitrogen atom ring member may be substituted with one substituent selected from W or may have empty valences satisfied by the ring itself.

In the compounds of the present invention, the "A" substituent heterocyclyl ring is attached to the 2 position of the imidazole scaffold via a ring carbon atom and a linking carbon atom. The ring carbon atom forms a double bond with the linking carbon atom. The heterocyclyl ring contains at least a single nitrogen heteroatom substituted with a substituent selected from W. The single nitrogen atom will be adjacent to the ring carbon atom of attachment. The ring carbon of attachment will also have an adjacent ring carbon.

For instant compounds of the invention, the carbon atom ring members that form the heterocyclyl ring "A" substituent are fully saturated except for the single carbon of attachment. Other compounds of the invention may have a partially unsaturated heterocyclyl ring that forms the "A" substituent. Preferred partially unsaturated heterocyclyl rings may contain one or two double bonds. Such compounds are not considered to be fully aromatic and are not referred to as heteroaryl compounds. Therefore, a five member heterocyclyl ring that forms the "A" substituent may optionally have a double bond formed in the ring between adjacent ring members; a six or seven member heterocyclyl ring that forms the "A" substituent may have two double bonds formed in the ring between adjacent ring members. The carbon ring member of attachment may stably form only a single bond with an adjacent carbon ring member and the first nitrogen ring member. The first nitrogen ring member substituted with a substituent selected from W links the carbon ring member of attachment to another ring member (which may be a carbon or a second nitrogen atom) and may stably form only a single bond with both ring members.

The term "alkylene" refers to a straight chain alkyl linking group. The term "alkylene" refers to a straight chain alkenyl linking group wherein one or two double bonds are formed in the chain between adjacent members. The term "heteroalkylene" refers to a straight chain alkyl linking group wherein at least one member is a heteroatom independently selected from the group consisting of nitrogen, oxygen and sulfur. The heteroalkylene chain may contain up to two heteroatoms. Similarly, the term "heteroalkenylene" refers to a straight chain alkenyl linking group wherein one or two double bonds are formed in the chain between adjacent chain members.

In particular, the "Y" substituent comprises a three to five member alkylene, alkenylene, heteroalkylene or heteroalkenylene chain optionally substituted with one to two substituents independently selected from X. Up to two carbon atom chain members may be optionally substituted with one to two substituents selected from X or may have empty valences satisfied by the ring itself. A nitrogen heteroatom chain member may be optionally substituted with one substituent selected from W or may have empty valences satisfied by the ring itself.

In the compounds of the present invention, the "Y" substituent is attached to an adjacent unsaturated carbon atom. The terminal atom of the "Y" substituent attached to the adjacent carbon atom is either a carbon atom or a heteroatom that forms a stable chemical bond within the "A" substituent heterocyclyl ring. The adjacent carbon atom forms a triple bond with a linking carbon atom whereby the "Y" substituent is attached to the 2 position of the imidazole scaffold. For instant compounds of the invention, the "Y" substituent is a fully saturated alkylene or heteroalkylene chain. Other compounds of the invention may have a partially unsaturated alkenylene or heteroalkenylene chain that forms the "Y" substituent. Preferred unsaturated chains may contain one or two double bonds.

The term aryl refers to a single aromatic ring of six carbon members or a bicyclic aromatic ring of ten carbon members. Examples of such aryl rings include phenyl and naphthyl.

The term heteroaryl refers to an aromatic ring of five or six members wherein the ring has at least one heteroatom member. Suitable heteroatoms include nitrogen, oxygen or sulfur. In the case of five-membered rings, the heteroaryl ring contains one member of nitrogen, oxygen or sulfur and, in addition, may contain up to two additional nitrogens. In the case of six-membered rings, the heteroaryl ring may contain from one to three nitrogen atoms. For the case wherein the six member ring has three nitrogens, at most two nitrogen atoms are adjacent.

In the present invention, the term "Michael addition" refers to the nucleophilic addition of a carbanion (such as the nitrogen portion of —N(H)(W) in a compound of Formula IV) to the β position of an α,β-unsaturated carbon-carbon bond (such as the 2 position of the triple bond portion of a compound of Formula IV), a process known to those skilled in the art.

As used in this invention the term "cytokine" refers to the proteins TNF-α and IL-1β. Cytokine related disorders are diseases of humans and other mammals where the overproduction of cytokines causes the symptoms of the disease. The overproduction of the cytokines, TNF-α and IL-1β has been linked to a number of diseases including, but not limited to, rheumatoid arthritis, inflammatory bowel disease, septic shock osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, acute pancreatitis, allograft rejection, allergic inflammation in the lung, atherosclerosis, multiple sclerosis, cachexia, Alzheimer's disease, stroke, Crohn's disease, inflammatory bowel disease, ischemia, congestive heart failure, pulmonary fibrosis, hepatitis, glioblastoma, Guillain-Barre Syndrome, and systemic lupus erythematosus.

The term "effective dose" refers to an amount of a compound of Formula I which reduces the amount of TNFα and/or IL-1β which may be detected in a mammal suffering from a cytokine mediated disorder. In addition, the term "effective dose" refers to an amount of a compound of Formula I which reduces the symptoms of a cytokine related disorder.

The term "FCS" represents fetal calf serum, "TCA" represents trichloroacetic acid and the "RPMI" represents the medium from the Roswell Park Memoria Inst. (Sigma cat #R0833). "SEM" refers to 2-(trimethylsilyl)ethoxymethyl) and "LDA" refers to lithium diisopropylamide. The symbol "Ph" refers to phenyl and "PHT" refers to phthalimido.

The compounds of the present invention may be prepared by the following scheme, which may produce more than one embodiment of the instant compounds. Such embodiments are intended to be included within the scope of this invention. U.S. Pat. No. 5,965,583 (heretofore incorporated by reference) and U.S. Pat. No. 6,040,320 (heretofore incorporated by reference) disclose schemes and procedures which may be used to prepare intermediates for use in the present invention. Compounds prepared from such intermediates are intended to be within the scope of this invention.

The compounds of the invention may be prepared as shown in Scheme A. Compound A1 to the Compound of Formula II depicted in Scheme A were produced according to the procedure described for Example 14 in U.S. Pat. No. 5,965,583. Other imidazoles, which may be prepared using the methods of the present invention, unsubstituted at the 1-position are subject to tautomerization; therefore, substituents for $R_1$ and $R_2$ may be interchangeable when $R_3$ is hydrogen.

Intermediate Compound A1 was synthesized according to the methodology of Lantos et. al. *J. Org. Chem.* 1988, 53, 4223–4227. Compound A1 was reacted with selenium dioxide ($SeO_2$) in dioxane at about 80° C. and afforded diketone Compound A2. Treatment of Compound A2 with phenylpropylamine, ammonium acetate and formaldehyde or a formaldehyde equivalent such as hexamethylenetetraamine in acetic acid at about 80–100° C. yielded imidazole Compound A3. The imidazole Compound A3 was iodinated by deprotonation at the number 2 carbon with a strong base such as lithium diisopropylamide (LDA) at about −20 to about −78° C. followed by addition of iodine to give the iodinated imidazole Compound A4. Compound A4 was then coupled with a compound of the formula —CC(Y)Cl; wherein Y is as defined herein, using a palladium (II) [Pd(II)] catalyst such as tetrakis tris(triphenylphosphine) palladium (II) in acetonitrile and excess triethylamine at 80° C. for 3–18 hours to obtain the intermediate Compound of Formula II. The Compound of Formula II was reacted with excess alkylamine $H_2N(W)$ in methanol at about 70° C. to about 80° C. for about 3 to about 18 hours (h) and resulted in a secondary amine intermediate which was then subjected to an intramolecular Michael addition to obtain the target Compound of Formula I.

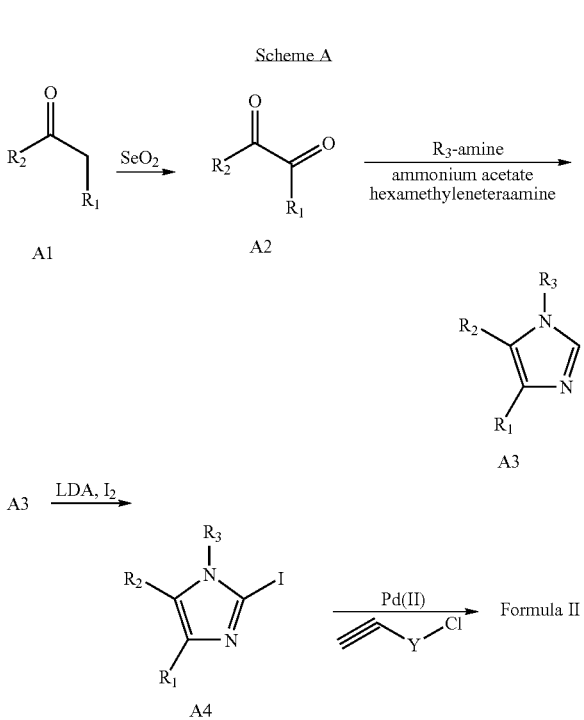

-continued

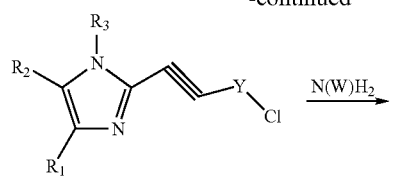

Formula II

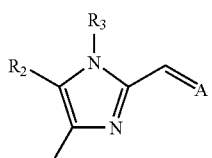

Formula I

Compounds of Formula I may be used in pharmaceutical compositions to treat patients (humans and other primates) with disorders related to the overproduction of inflammatory cytokines, particularly TNF-α. The preferred route is oral administration, however compounds may be administered by intravenous infusion or topical administration. Oral doses range from about 0.01 to 100 mg/kg, daily. Some compounds of the invention may be orally dosed in the range of about 0.01 to about 50 mg/kg daily, while others may be dosed at 0.01 to about 20 mg/kg daily. Infusion doses can range from about 1.0 to $1.0 \times 10^4$ µg/kg/min of inhibitor, admixed with a pharmaceutical carrier over a period ranging from several minutes to several days. For topical administration compounds of Formula I may be mixed with a pharmaceutical carrier at a concentration of about 0.1 % to about 10% of drug to vehicle.

The novel compounds of Formula I and pharmaceutical compositions thereof of this invention inhibit the in vitro activity of p-38 in the nanomolar range. In addition, the compounds and pharmaceutical compositions thereof inhibit the in vitro secretion of TNF-α and IL-1β in the nanomolar range. Animal models demonstrate the inhibition of LPS induced TNF-α, as well as the inhibition of rheumatoid arthritis.

With this range of activity, the compounds and associated pharmaceutical compositions of the invention are useful in the treatment of a variety of cytokine related disorders including, but no limited to, rheumatoid arthritis, inflammatory bowel disease, septic shock osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, acute pancreatitis, allograft rejection, allergic inflammation in the lung, atherosclerosis, multiple sclerosis, cachexia, Alzheimer's disease, stroke, Crohn's disease, inflammatory bowel disease, ischemia, congestive heart failure, pulmonary fibrosis, hepatitis, glioblastoma, Guillain-Barre Syndrome, and systemic lupus erythematosus.

Pharmaceutical compositions of the present invention can be prepared using conventional pharmaceutical excipients and compounding techniques. Oral dosage forms may be elixirs, syrups, capsules tablets and the like. Where the typical solid carrier is an inert substance such as lactose, starch, glucose, methyl cellulose, magnesium stearate, dicalcium phosphate, mannitol and the like; and typical liquid oral excipients include ethanol, glycerol, water and the like.

All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

In order to illustrate the invention the following examples are included. These examples do not limit the invention. They are only meant to suggest a method of practicing the invention. Those skilled in the art may find other methods of practicing the invention, which are readily apparent to them. However those methods are deemed to be within the scope of this invention.

SYNTHETIC EXAMPLES

Example 1

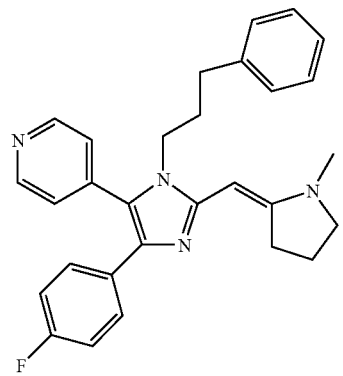

4-[4-(4-fluorophenyl)-2-[(E)-(1-methyl-2-pyrrolidinylidene)methyl]-1-(3-phenylpropyl)-1H-imidazol-5-yl]-pyridine (Compound 1)

The starting material for Compound 1 was prepared as illustrated by the procedure used for Compound 14, found in U.S. Pat. No. 5,965,583. Compound 14 (1.39 grams, 3.04 mmol) was placed in a tube and a 2N solution of methylamine (15 mL) and 4-dimethylaminopyridine (5 mol%) was added. The tube was sealed and placed in an oil bath heated to about 70° C. for about 24 h. The tube was removed from the oil bath and allowed to cool to ambient temperature before being opened. The mixture was evaporated in vacuo and the crude product was purified by column chromatography (silica gel) using a mobile phase consisting of methylene chloride:methanol in a 19:1 (v/v) ratio and afforded Compound 1 which was recrystallized from ethyl acetate-hexane; m.p. 171–172° C.; MS 453 (MH$^+$). $^1$H NMR (CDCl$_3$) δ 8.59 (d, 2H) 4.52 (s, 1H, exch.), 2.75 (s, 3H, CH$_3$).

Example 2

4-[4-(4-fluorophenyl)-2-[(E)-(1-ethyl-2-pyrrolidinylidene)methyl]-1-(3-phenylpropyl)-1H-imidazol-5-yl]-pyridine (Compound 2)

Following the procedure of Example 1 and substituting the appropriate starting materials, compounds and reagents, Compound 2 was also prepared; m.p. 126.6–127.6° C.; MS 467 (MH$^+$).

BIOLOGICAL EXAMPLES

As discussed previously, agents which inhibit the activity of the enzyme p38, inhibit the production of the inflammatory cytokines TNF-α and IL-1. The biological activity of the compounds of the present invention was demonstrated by in vitro and in vivo assays.

Example 3

Compounds of the invention were measured for their ability to inhibit the activity of p38 in an in vitro whole cell assay using peripheral blood mononuclear cells ("PBMC") obtained from human blood as follows. Freshly obtained venous blood was anticoagulated with heparin, diluted with an equal volume of phosphate buffered saline ("PBS") and placed in a sterile tube or other container. Aliquots (30 mL) of this mixture were transferred to centrifuge tubes which were underlaid with Ficoll-Hypaque (15 mL). The prepared tubes were centrifuged at 400×g without braking for 30 min at room temperature. Approximately ½ to ⅔ of the platelet layer above the mononuclear cell band was removed with a pipet. The majority of the mononuclear cell layer was carefully removed using a pipet and these PBMCs were diluted with PBS and spun at 600×g for 15 min. The resulting PBMCs were washed with another portion of PBS and spun at 400×g for 10 min at room temperature. The recovered pellets were diluted in low endotoxin RPMI/1% FCS culture medium and gave a cell concentration of 0.5–2.0×10$^6$ PMBC/mL. A small volume of the suspension was removed for counting on a hemocytometer and the remaining preparation was centrifuged at 200×g for 15 min at room temperature. The recovered pelleted PMBC were resuspended in RPMI/1% FCS to a concentration of 1.67×10$^6$/mL.

To run the assay, the PBMC suspension (180 μL) was transferred to duplicate wells of a 96-well flat-bottom microtiter plate and incubated for 1 h at 37° C. A solution of test compound (10 μL: prepared at 20× the desired final concentration) was added to each well and the plate was incubated for 1 h at 37° C. A solution (10 μL) of LPS in RPMI/1% FCS (200 ng/mL) was added and the wells were incubated overnight at 37° C. The supernate (100 μL) was removed from each well and diluted with RPMI/1% FCS (400 μL). The samples were analyzed for TNF-α using a commercial ELISA kit (Genzyme), resulting in data as shown in Table A.

Example 4

The ability of the compounds of Formula I to inhibit LPS induced TNF-α production was demonstrated in the following in vivo rodent assay. Mice (BALB/cJ females, Jackson Laboratories) or rats (Lewis males, Charles River) were fasted for 30 min prior to oral dosing with 5–10 mL/kg of test compound at 5–50 mg/kg. Thirty minutes after dosing, the animals were injected intraperitoneally with LPS at 1 mg/kg and returned to their cages for 1 h. Animals were anesthetized by $CO_2$, exsanguinated by cardiac puncture and whole blood collected (0.1–0.7 mL). The blood was allowed to clot and serum was transferred to a centrifuge tube. This sample was centrifuged, serum was collected, aliquoted and frozen at −80 C. Samples were tested by commercial ELISAs for TNF-α (Endogen for mouse TNF-α and Biosource for rat TNF-α), resulting in data as shown in Table A.

TABLE A

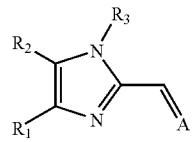

| Cpd | W | TNF-α IC$_{50}$ (nM) | % Inhibition Mouse TNF-α 25 mg/kg | 10 mg/kg |
|---|---|---|---|---|
| 1 | methyl | 15 | 99 | 77 |
| 2 | ethyl | 17 | 98 | 89 |

What is claimed is:
1. A compound of Formula I

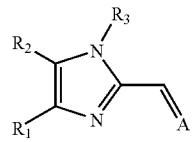

Formula I wherein:
R$_1$ is selected from the group consisting of phenyl (optionally substituted with one to five substituents independently selected from the group consisting of C$_{1-5}$alkyl, halogen, nitro, trifluoromethyl and nitrile) and heteroaryl (wherein heteroaryl contains 5 to 6 ring atoms);

R$_2$ is selected from the group consisting of phenyl (optionally substituted with one to five substituents independently selected from the group consisting of C$_{1-5}$alkyl, halogen, nitro, trifluoromethyl and nitrile) and heteroaryl (wherein heteroaryl contains 5 to 6 ring atoms and is optionally substituted with one to four substituents independently selected from the group consisting of C$_{1-5}$alkyl and halogen);

R$_3$ is selected from the group consisting of hydrogen, C$_{1-5}$alkyl, arylC$_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl)), heteroaryl$C_{1-5}$alkyl (wherein heteroaryl contains 5 to 6 ring atoms), amino$C_{1-5}$alkyl, diamino$C_{1-5}$alkyl, phthalimido$C_{1-5}$alkyl, succinimido$C_{1-5}$alkyl, SEM, $C_{1-5}$alkylcarbonyl, $C_{1-5}$alkylcarbonyl$C_{1-5}$alkyl, $C_{1-5}$alkoxycarbonyl, arylcarbonyl, aryloxycarbonyl, aryl$C_{1-5}$alkyloxycarbonyl and aryfoxycarbonyl$C_{1-5}$alkyl;

A is a five to seven member heterocyclyl ring optionally substituted with one to two substituents independently selected from X; wherein the ring has an unsaturated bond of attachment at a ring carbon atom; has a ring nitrogen atom substituted with a substituent selected from W adjacent to the ring carbon of attachment; has a ring carbon atom adjacent to the ring carbon of attachment; optionally has 1 or 2 double bonds formed in the ring between adjacent ring members; and, optionally has 1 or 2 ring members independently selected from the group consisting of O, N and S;

W is a substituent selected from the group consisting of hydrogen, $C_{1-5}$alkyl, $C_{1-5}$alkoxy, amino$C_{1-5}$alkyl (wherein amino is optionally substituted with one to two substituents independently selected from $C_{1-5}$alkyl), aryl$C_{1-5}$alkyl and heteroaryl$C_{1-5}$alkyl (wherein the aryl, heteroaryl and $C_{1-5}$alkyl portions of any of the foregoing substituents are optionally substituted with one to three substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile); and, X is a substituent selected from the group consisting of $C_{1-5}$alkyl, $C_{2-5}$alkenyl, $C_{2-5}$alkynyl, $C_{1-5}$alkoxy, amino (wherein amino is optionally substituted with one to two substituents independently selected from $C_{1-5}$alkyl), amino$C_{1-5}$alkyl (wherein amino is optionally substituted with one to two substituents independently selected from $C_{1-5}$alkyl), aryl, aryl$C_{1-5}$alkyl, heteroaryl and heteroaryl$C_{1-5}$alkyl (wherein the aryl, heteroaryl and $C_{1-5}$alkyl portions of any of the foregoing substituents are optionally substituted with one to two substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile);

and pharmaceutically acceptable salts thereof.

2. A compound of claim 1 wherein $R_1$ is phenyl (optionally substituted with one to five substituents independently selected from the group consisting of $C_{1-5}$alkyl and halogen).

3. A compound of claim 2 wherein $R_1$ is phenyl substituted with a substituent selected from halogen.

4. A compound of claim 3 wherein $R_1$ is phenyl substituted with fluorine.

5. A compound of claim 1 wherein $R_2$ is heteroaryl (wherein heteroaryl contains 5 to 6 ring atoms and is optionally substituted with one to four substituents independently selected from the group consisting of $C_{1-5}$alkyl and halogen).

6. A compound of claim 5 wherein $R_2$ is selected from the group consisting of 2-furyl, 3-furyl, 2-thienyl, 3-thienyl, 2-pyrrolyl, 3-pyrrolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 3-pyrazolyl, 4-pyrazolyl, 5-pyrazolyl, 3-isoxazolyl, 4-isoxazolyl, 5-isoxazolyl, 3-isothiazolyl, 4-isothiazolyl, 5-isothiazolyl, 4-1,2,3-oxadiazolyl, 5-1,2,3-oxadiazolyl, 4-1,2,3-triazolyl, 5-1,2,3-triazolyl, 2-1,3,4-thiadiazolyl, 5-1,3,4-thiadiazolyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 3-pyrazinyl and 2-1,3,5-triazinyl optionally substituted with one substituent selected from $C_{1-5}$alkyl.

7. A compound of claim 6 wherein $R_2$ is selected from the group consisting of 4-pyridinyl, 4-pyrimidinyl and (2-butyl) pyridin-4-yl.

8. A compound of claim 1 wherein $R_3$ is selected from the group consisting of hydrogen, $C_{1-5}$alkyl and aryl$C_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl)).

9. A compound of claim 8 wherein $R_3$ is selected from the group consisting of hydrogen and phenyl$C_{1-5}$alkyl (wherein phenyl is optionally substituted with one substituent selected from $C_{1-5}$alkoxy).

10. A compound of claim 9 wherein $R_3$ is selected from the group consisting of benzyl, phenethyl and phenylpropyl.

11. A compound of claim 1 wherein A is selected from the group consisting of pyrrolidinyl, imidazolidinyl, pyrazolidinyl, piperidinyl, morpholinyl, thiomorpholinyl, piperazinyl, hexahydro-1H-azepine, hexahydro-1H-1,3-diazepine, hexahydro-1,3-oxazepine, hexahydro-1,3-thiazepine and hexahydro-1H-1,3,5-triazepine.

12. A compound of claim 11 wherein A is selected from the group consisting of pyrrolidinyl, imidazolidinyl, pyrazolidinyl, piperidinyl and piperazinyl.

13. A compound of claim 1 wherein W is a substituent selected from the group consisting of hydrogen, $C_{1-5}$alkyl and $C_{1-5}$alkoxy (wherein $C_{1-5}$alkyl for any of the foregoing substituents is optionally substituted with one to three substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile).

14. A compound of claim 13 wherein W is a substituent selected from the group consisting of hydrogen and $C_{1-5}$alkyl.

15. A compound of claim 14 wherein W is a substituent selected from the group consisting of hydrogen, methyl, ethyl, n-propyl, i-propyl, n-butyl and t-butyl.

16. A compound of claim 1 wherein X is a substituent selected from the group consisting of $C_{1-5}$alkyl, $C_{2-5}$alkenyl, $C_{2-5}$alkynyl, $C_{1-5}$alkoxy and amino (wherein amino is optionally substituted with one to two substituents independently selected from $C_{1-5}$alkyl).

17. A compound of claim 16 wherein X is a substituent selected from $C_{1-5}$alkyl.

18. A compound of claim 17 wherein X is a substituent selected from the group consisting of methyl, ethyl, n-propyl, i-propyl, n-butyl and t-butyl.

19. A compound of claim 1 selected from

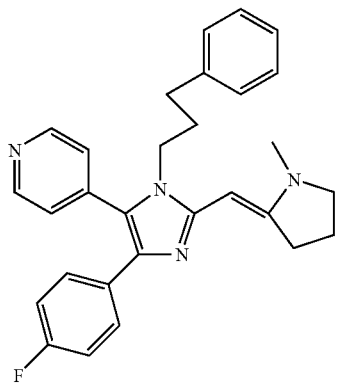

and pharmaceutically acceptable salts thereof.

20. A compound of claim 1 selected from

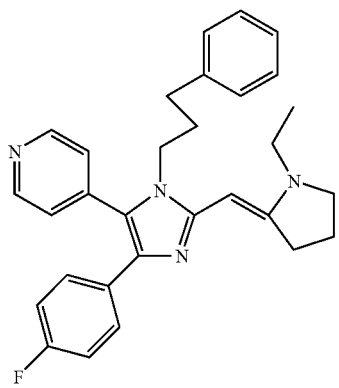

and pharmaceutically acceptable salts thereof.

21. A method for preparing a compound of Formula I

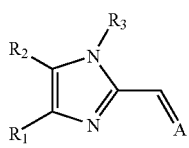

Formula I wherein
- $R_1$ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms);
- $R_2$ is selected from the group consisting of phenyl (optionally substituted with one to five substituents independently selected from the group consisting of $C_{1-5}$alkyl, halogen, nitro, trifluoromethyl and nitrile) and heteroaryl (wherein heteroaryl contains 5 to 6 ring atoms and is optionally substituted with one to four substituents independently selected from the group consisting of $C_{1-5}$alkyl and halogen);
- $R_3$ is selected from the group consisting of hydrogen, $C_{1-5}$alkyl, aryl$C_{1-5}$alkyl (wherein aryl is optionally substituted with one to four substituents independently selected from the group consisting of $C_{1-5}$alkyl, $C_{1-5}$alkoxy, halogen and amino (wherein amino is optionally substituted with one to two substituents independently selected from $C_{1-5}$alkyl)), heteroaryl$C_{1-5}$alkyl (wherein heteroaryl contains 5 to 6 ring atoms), amino$C_{1-5}$alkyl, diamino$C_{1-5}$alkyl, phthalimido$C_{1-5}$alkyl, succinimido$C_{1-5}$alkyl, SEM, $C_{1-5}$alkylcarbonyl, $C_{1-5}$alkylcarbonyl$C_{1-5}$alkyl, $C_{1-5}$alkoxycarbonyl, arylcarbonyl, aryloxycarbonyl, aryl$C_{1-5}$alkyloxycarbonyl and aryloxycarbonyl$C_{1-5}$alkyl;
- A is a five to seven member heterocyclyl ring optionally substituted with one to two substituents independently selected from X; wherein the ring has an unsaturated bond of attachment at a ring carbon atom; has a ring nitrogen atom substituted with a substituent selected from W adjacent to the ring carbon of attachment; has a ring carbon atom adjacent to the ring carbon of attachment; optionally has 1 or 2 double bonds formed in the ring between adjacent ring members; and, optionally has 1 or 2 ring members independently selected from the group consisting of O, N and S;
- W is a substituent selected from the group consisting of hydrogen, $C_{1-5}$alkyl, $C_{1-5}$alkoxy, amino$C_{1-5}$alkyl (wherein amino is optionally substituted with one to two substituents independently selected from $C_{1-5}$alkyl), aryl$C_{1-5}$alkyl and heteroaryl$C_{1-5}$alkyl (wherein the aryl, heteroaryl and $C_{1-5}$alkyl portions of any of the foregoing substituents are optionally substituted with one to three substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile);
- X is a substituent selected from the group consisting of $C_{1-5}$alkyl, $C_{2-5}$alkenyl, $C_{2-5}$alkynyl, $C_{1-5}$alkoxy, amino (wherein amino is optionally substituted with one to two substituents independently selected from $C_{1-5}$alkyl), amino$C_{1-5}$alkyl (wherein amino is optionally substituted with one to two substituents independently selected from $C_{1-5}$alkyl), aryl, aryl$C_{1-5}$alkyl, heteroaryl and heteroaryl$C_{1-5}$alkyl (wherein the aryl, heteroaryl and $C_{1-5}$alkyl portions of any of the foregoing substituents are optionally substituted with one to two substituents independently selected from the group consisting of halogen, $C_{1-5}$alkyl, $C_{1-5}$alkoxy, aryl, heteroaryl, amino (wherein amino is optionally substituted with one to two substituents independently selected from $C_{1-5}$alkyl) and nitrile);

and pharmaceutically acceptable salts thereof; comprising, converting an intermediate compound of Formula II

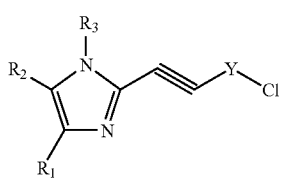

Formula II wherein
- Y is a three to five member linear alkylene, alkenylene, heteroalkylene or heteroalkenylene chain optionally substituted with one to two substituents independently selected from X; wherein the alkenylene and heteroalkenylene chain has 1 or 2 double bonds formed in the chain between adjacent members; and, wherein the heteroalkylene and heteroalkenylene chain has 1 or 2 members independently selected from the group consisting of O, N and S; and, all other substituents are as previously defined;

by ammonolysis, using an excess of a compound selected from H$_2$N(W) in an appropriate solvent, to form a secondary amine intermediate of Formula III; and,

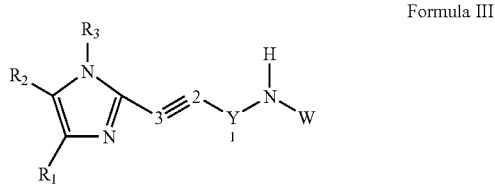

Formula III coupling the amine at the 2 position of the triple bond by a Michael addition, in the presence of appropriate reagents and solvents, to form the compound of Formula I.

22. The method of claim 21 wherein Y is a three to five member linear alkylene chain optionally substituted with one to two substituents independently selected from X.

23. The method of claim 22 wherein Y is an unsubstituted three to five member linear alkylene chain.

24. A pharmaceutical composition comprising a compound according to claim 1 and a pharmaceutically acceptable carrier or diluent.

25. A pharmaceutical composition comprising a compound according to claim 19 and a pharmaceutically acceptable carrier or diluent.

26. A pharmaceutical composition comprising a compound according to claim 20 and a pharmaceutically acceptable carrier or diluent.

27. A method for treating inflammatory diseases comprising administering a compound of claim 1 to a mammal suffering from an inflammatory disease at an effective dose.

28. A method for treating inflammatory diseases comprising administering a pharmaceutical composition of claim 24 to a mammal suffering from an inflammatory disease at an effective dose.

29. The method of claim 27 wherein the compound is administered orally and the effective dose is from about 0.1 mg/kg/day to about 100 mg/kg/day.

30. The method of claim 29 wherein the effective dose is from about 0.1 mg/kg/day to about 50 mg/kg/day.

31. The method of claim 27 wherein the inflammatory disease is arthritis.

32. The method of claim 31 wherein the compound is administered orally and the effective dose is from about 0.1 mg/kg/day to about 100 mg/kg/day.

33. The method of claim 32 wherein the effective dose is from about 0.1 mg/kg/day to about 50 mg/kg/day.

* * * * *